United States Patent
Van Blarcom et al.

(10) Patent No.: US 8,747,918 B2
(45) Date of Patent: Jun. 10, 2014

(54) PLANT ESSENTIAL OIL-BASED ANTIMICROBIAL FISH FILMING COMPOSITIONS AND METHODS OF USE

(71) Applicant: Sergeant's Pet Care Products Inc., Omaha, NE (US)

(72) Inventors: Ralph Van Blarcom, Land O'Lakes, FL (US); Colin G. Brodie, La Vista, NE (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

(21) Appl. No.: 13/944,667

(22) Filed: Jul. 17, 2013

(65) Prior Publication Data

US 2013/0302451 A1   Nov. 14, 2013

Related U.S. Application Data

(62) Division of application No. 13/336,577, filed on Dec. 23, 2011, now Pat. No. 8,512,766.

(60) Provisional application No. 61/428,091, filed on Dec. 29, 2010.

(51) Int. Cl.
*A61K 36/00* (2006.01)

(52) U.S. Cl.
USPC .......................................................... 424/725

(58) Field of Classification Search
None
See application file for complete search history.

(56) References Cited

U.S. PATENT DOCUMENTS

| 5,593,678 | A  | 1/1997  | Evans et al. |
| 2005/0230871 | A1 | 10/2005 | Bess |
| 2009/0239907 | A1 | 9/2009  | Bridges et al. |
| 2010/0092398 | A1 | 4/2010  | Reynolds |
| 2010/0297316 | A1 | 11/2010 | Gutzmann et al. |
| 2010/0311759 | A1 | 12/2010 | Kawano et al. |

FOREIGN PATENT DOCUMENTS

JP   06287125 A   10/1994

OTHER PUBLICATIONS http://www.apifishcare.com/Products/Product.aspx?ProductID=56 , 2012.
http://www.apifishcare.com/products/product.aspx?productID=57 , 2012.

*Primary Examiner* — Qiuwen Mi
(74) *Attorney, Agent, or Firm* — Polsinelli PC

(57) ABSTRACT

Novel plant essential oil-based antimicrobial filming compositions that are useful in protecting, repairing and strengthening the natural slime coat found on fish are disclosed, which compositions are comprised of a mixture of plant essential oils having antimicrobial properties, filming agents, and surfactants.

15 Claims, No Drawings

PLANT ESSENTIAL OIL-BASED ANTIMICROBIAL FISH FILMING COMPOSITIONS AND METHODS OF USE

CROSS-REFERENCE TO RELATED APPLICATIONS

This patent application is a divisional of U.S. Ser. No. 13/336,577, filed Dec. 23, 2011, which claims the benefit of U.S. Provisional Application Ser. No. 61/428,091, filed on Dec. 29, 2010. Both applications are herein incorporated by reference in their entirety.

FIELD OF THE INVENTION

The present disclosure describes antimicrobial filming compositions for fish which are comprised of at least one plant essential oil, a filming agent, and a surfactant. The compositions protect, repair, and strengthen the natural slime coat found on fish by trapping the essential oils around a fish's body, thereby forming a shield against bacterial/fungicidal, parasitical, and protozoan infections.

BACKGROUND OF THE INVENTION

Fish secrete a mucoprotein protective slime coat that covers the scales and skin. This slime coat acts as a defense against invasion by bacterial, parasitic, protozoan, and fungal pathogens. The slime coating contains enzymes and antibodies to fight infection and acts as a shield against disease causing organisms in the fish's external environment. The slime coating also acts as a barrier to prevent loss of internal electrolytes and body fluids.

Stress is the most common cause of a deteriorated slime coat, the other cause being mechanical damage. Stress on fish can be caused by a number of common factors, including poor water quality (e.g. improper pH, salinity, etc.), water temperature fluctuations, water changes, fish incompatibility, transportation, netting/handling the fish, and infection/disease.

When a fish is netted, handled or placed in a stressful situation, for example in an environment having low oxygen, high carbon dioxide or temperature fluctuations, the slime coating is disturbed, making the fish vulnerable to disease, such as bacterial, fungal and parasitic diseases. Moreover, ammonia, a waste product of fish's digestion and respiration, is released into the water containing fish. Ammonia is also released at high levels by dead fish and decaying food. At high ammonia levels, the fish are subject to ammonia burns which disturb the slime coating and adversely affect the fish.

Water treatment conditioners are currently being used in the art to help build up or maintain a fish's slime coat. These products typically comprise plant essential oils, either alone or a combination thereof, and work by eliminating the stresses in the aquatic environment, which have a negative effect on a fish's slime coat. The major drawback to this technology is that the fish are only treated if they are in the treated water. The essential oils are dispensed into the water and penetrate the fish's body, but the products do not contain any additional component for sealing the oils onto the body of the fish. Unfortunately, with these types of treatments, once the fish are removed from the treated habitat their slime coat is once again vulnerable to stress and degradation, and ultimately, bacteria, parasites, and fungal pathogens.

Another treatment currently being used in the art involves the use of what is referred to as bio-sphere technology. These products contain antibiotics encapsulated within microscopic bio-spheres. The spheres attach to the fish's body and breakdown over time. As the spheres breakdown, the antibiotics are released from within the spheres to topically treat the fish. There are several problems with using the sphere-based products to protect fish. First, the products currently on the market encapsulate synthetic antibiotics, such as Sulfadimidine and trimethoprin. Synthetic antibiotics are strong medications that can potentially harm certain fish. In addition, the products available on the market are only capable of treating bacterial and fungal infections. These infections are only two possible types of infections to which fish can be susceptible. Finally, it is difficult to obtain instantaneous and complete coverage of a fish's body by using the bio-spheres. The spheres breakdown over time thereby delaying treatment of the fish. This delay in treatment could have the effect of possibly exacerbating the infection affecting the fish. Also, because the spheres can vary in shape and size, their breakdown following attachment to the fish can result in incomplete coverage of the fish's entire body.

Therefore, there exists a need for the development of a new treatment for the prevention and maintenance of a fish's slime coat to keep the fish safe from harmful pathogens and infestations, which treatment (1) directly treats the fish's body and not the fish's environment, (2) contains plant essential oils instead of harsh synthetic chemicals, (3) provides protection for a fish against all types of infections, and (4) provides instantaneous and complete coverage of a fish's body to treat and protect the fish from infections.

Because of the above described problems in the prior art, there is a widely felt need for new products to treat a fish's slime coat and protect fish from bacterial, fungal, protozoan, and parasitic infestations.

SUMMARY OF THE INVENTION

The present disclosure is directed to novel plant essential oil-based antimicrobial fish filming compositions that are useful in protecting, repairing and strengthening the natural slime coat found on a variety of aquatic animals, namely fish. The compositions disclosed herein are comprised of a mixture of plant essential oils having antimicrobial properties, filming agents, and surfactants. When the composition is dispensed into the aquatic environment by dropper, the plant essential oils penetrate and are absorbed into a fish's body, while the filming agents completely surround and coat the fish's body to trap in the oils. The filming agents help the oils to penetrate into the cell structure of the natural slime coat and fish's body. The resultant film coat protects the fish by mimicking the fish's natural slime coat in order to protect the fish from infections. The antimicrobial compositions disclosed herein include bactericidal compositions (which include fungicidal compositions), parasitical compositions, and protozoan compositions.

In one embodiment, the antimicrobial composition of the present disclosure comprises from about 1% to about 1.6% (% w/w) of a mixture of plant essential oils, between about 0.1% and about 5% (% w/w) of a filming/plasticizing agent, and between about 3% and about 5% (% w/w) of a surfactant.

In another embodiment, the antimicrobial composition is a bactericidal and fungicidal composition, which preferably comprises between about 1.1% and about 1.3% (% w/w) of a mixture of plant essential oils, between about 0.1% and about 5% (% w/w) of a filming agent, and between about 3% and about 5% (% w/w) of a surfactant.

In another embodiment, the antimicrobial composition is a protozoical composition, which comprises between about 1.1% and about 1.3% (% w/w) of a mixture of plant essential oils, between about 0.1% and about 5% (% w/w) of a filming agent, and between about 3% and about 5% (% w/w) of a surfactant.

In another embodiment, the antimicrobial composition is a parasitical composition, which comprises between about 1.3% and about 1.5% (% w/w) of a mixture of plant essential oils, between about 0.1% and about 5% (% w/w) of a filming agent, and between about 3% and about 5% (% w/w) of a surfactant.

The present disclosure is also directed to a method for preventing antimicrobial infections (which includes bacterial infections, fungal infections, parasitical infections, and protozoan infections) in fish, the method comprising dispensing an antimicrobial composition into an aquatic environment, wherein the composition is comprised of a mixture of plant essential oils, a filming agent, a plasticizer, and a surfactant.

DETAILED DESCRIPTION OF THE PREFERRED EMBODIMENTS

The antimicrobial composition provided herein has been shown to mimic a fish's natural slime coat and protect the fish from stresses that can degrade the slime coat and make the fish susceptible to a variety of infections, including bacterial, fungal, parasitical, and protozoan. The composition of the present disclosure comprises a mixture of plant essential oils and extracts combined with filming agents and other components that attract to the body of a fish and form a shield around the body, thereby sealing the essential oils onto the body of the fish. This shield then acts as a treatment or as an expellant to prevent water borne pathogens from attacking or infecting the fish.

A basic antimicrobial composition comprises at least about 1% (% w/w) of a mixture of at least two plant essential oils and at least about 0.1% (% w/w) of a filming agent. Preferably, the basic antimicrobial composition comprises between about 1% and 1.6% (% w/w) of a mixture of at least two plant essential oils, between about 0.1% and 5% (% w/w) of a filming agent, and between about 3% and about 5% (% w/w) of a surfactant.

The term "fish" as used herein refers to substantially any species or varieties of fish which are confined in a reasonable space, such as for example, for breeding, holding, shipping, or as pets. Typically, the fish treated in accordance with the present invention would be held in aquariums of various sizes. It is believed to be economically impractical to protect fish in accordance with the present invention when fish are contained in a large lake, river, or other such body of water. However, fish contained in breeding ponds are specifically included herein. The term "fish" further includes both saltwater fish and freshwater fish.

I. Plant Essential Oils

Plant essential oils (also called volatile oils) are aromatic volatile oily liquids obtained from plant materials (flowers, buds, seeds, leaves, twigs, bark, herbs, wood, fruits and roots). They can be obtained by expression, fermentation or extraction but the method of steam distillation is most commonly used for commercial production. Chemically they are derived from terpenes, which constitute several thousand compounds with multiple functionalized molecules. The term "plant essential oil," as used herein, refers to a monocyclic, carbocyclic ring structure having six-members and substituted by at least one oxygenated or hydroxyl functional moiety.

Plant essential oils are a rich source of biologically active compounds and their antimicrobial properties have been known for many centuries. Essential oils have been used medicinally to kill bacteria, fungi, and viruses. Scientific research has documented that most viruses, fungi, and bacteria cannot live in the presence of many essential oils. Any plant essential oil having antimicrobial properties can be used in the compositions of the present disclosure. Suitable plant essential oils include, but are not limited to, members selected from the group consisting of Allspice, Aniseed, Basil, Bay, Benzoin, Bergamot, Black pepper, Cajuput, Chamomile, Camphor, Caraway, Carrot seed, Cassia, Cedarwood, Chamomile, Cinnamon, Citronella, Clary sage, Clove, Coriander, Cypress, Dill, Eucalyptus, Fennel, Frankincense, Geranium, Ginger, Grapefruit, Helichrysum, Hyssop, Jasmine, Juniper, Lavandin, Lavender, d-Limonene, Lemongrass, Lemon verbena, Lime, Mandarin, Marjoram, Melissa, Myrrh, Neroli, Niaouli, Nutmeg, Orange, Palma rosa, Patchouli, Peppermint, Petitgrain, Pimento, Pine, Rose, Rose geranium, Rosemary, Rosewood, Sage, Sandalwood, Spearmint, Tagetes, Tangerine, Thyme, Tea tree (Manuka), Vetiver, Wintergreen, Ylang-ylang, Rosehip oil, Baobab oil, Manila oil, and Neem oil. Preferably, essential oils are volatile and may be chosen without limitation from geranium, tea tree, pine, neem, d-Limonene, rosemary, cinnamon, or combinations thereof.

As discussed herein, the composition of the present invention will generally comprise, as one of the components, at least one plant essential oil and preferably will comprise a mixture of at least two or more plant essential oils. Typically, the amount of plant essential oil and the selection of plant essential oil present in the composition can and will vary depending on the particular infection the composition has been formulated to treat. By way of example, the concentration of plant essential oil present in the composition may be about 0.1% (% w/w), 0.2% (% w/w) 0.3% (% w/w), 0.4% (% w/w), 0.5% (% w/w), 1% (% w/w), 1.1% (% w/w), 1.2% (% w/w), 1.3% (% w/w), 1.4% (% w/w), 1.5% (% w/w), 1.6% (% w/w), 1.7% (% w/w), 1.8% (% w/w), 1.9% (% w/w), or 2% (% w/w). In one embodiment, the amount of plant essential oil present in the composition may range between about 0.1% and about 2% (% w/w). In another embodiment, the amount of plant essential oil present in the composition may range between about 0.5% and about 1.8% (% w/w). In an additional embodiment, the amount of plant essential oil present in the composition may range between about 1% and about 1.3% (% w/w).

In one embodiment, the antimicrobial composition is a bactericidal and fungicidal composition wherein the plant essential oil is selected from the group consisting of d-Limonene, pine oil, geranium oil, rosemary oil, cinnamon oil, and combinations thereof. Generally, for a bacterial and fungicidal composition, the plant essential oil comprises between about 0.1% and about 2% (% w/w) and preferably comprises between about 0.5% and about 1.8% (% w/w) of the composition. In a preferred embodiment, the bactericidal and fungicidal composition comprises between about 0.3% and about 0.5% (% w/w) d-Limonene, between about 0.1% and about 0.3% (% w/w) pine oil, between about 0.1% and about 0.3% (% w/w) geranium oil, between about 0.1% and about 0.3% (% w/w) rosemary oil, and between about 0.1% and about 0.3% (% w/w) cinnamon oil.

In another embodiment, the antimicrobial composition is a parasitical composition wherein the plant essential oil is selected from the group consisting of d-Limonene, neem oil, tea tree oil, capsaicin oil, and combinations thereof. Generally, for a parasitical composition, the plant essential oil comprises between about and preferably comprises between about 0.1% and about 2% (% w/w) and preferably comprises between about 0.5% and about 1.8% (% w/w) of the composition. In a preferred embodiment, the parasitical composition comprises between about 0.3% and about 0.5% (% w/w) d-Limonene, between about 0.3% and about 0.5% (% w/w) neem oil, between about 0.3% and about 0.5% tea tree oil (manuka oil), and between about 0.01% and about 0.2% capsaicin oil.

In another embodiment, the antimicrobial composition is a protozoical composition wherein the plant essential oil is selected from the group consisting of d-Limonene, neem oil, tea tree oil, and combinations thereof. Generally, for a protozoical composition, plant essential oil comprises between about 0.1% and about 2% (% w/w) and preferably comprises between about 0.5% and about 1.8% (% w/w) of the composition. In a preferred embodiment, the protozoical composition comprises between about 0.3% and about 0.5% (% w/w) d-Limonene, between about 0.3% and about 0.5% (% w/w) neem oil, and between about 0.3% and about 0.5% (% w/w) tea tree oil (manuka oil).

II. Filming Agent

The compositions of the present disclosure additionally comprise a filming agent, or a polymer, to hold or adhere the plant essential oil around the body of a fish, thereby forming a protective shield around the entire body of the fish. The filming agent also helps to prepare the cells at the surface of the fish skin to allow the passage of materials into it. Accordingly, the incorporation of a filming agent as disclosed herein enables the composition of the present invention to treat the entire fish directly and completely, instead of only treating the water or certain areas of the fish as previously done in the art.

Polymers are typically used as filming agents and the vast majority of the polymers used in film coating are either cellulose derivatives, such as cellulose ethers, or acrylic polymers and copolymers. Occasionally encountered are high molecular weight polyethylene glycols, polyvinyl pyrrolidone, polyvinyl alcohol and waxy materials. Any polymer having film forming and plasticizing properties can be used as a filming agent in the composition of the present disclosure. Suitable filming agents are known in the art and include members selected from the group consisting of hydroxypropyl methyl cellulose, chitosan, triethylene glycol (TEG), polyvinylpyrrolidone, polyvinyl alcohol-polyethylene glycol copolymers, basic polymethacrylate and combinations thereof. In one embodiment, the composition comprises a single filming agent. In another embodiment, the composition comprises two filming agents. In yet another embodiment, the composition comprises three or more filming agents. Preferably, the composition comprises a combination of three filming agents, which are chitosan, triethylene glycol, and polyvinylpyrrolidone.

Typically, the filming agent comprises at least about 0.05% (% w/w), 0.1% (% w/w), 0.2% (% w/w), 0.3% (% w/w), 0.4% (% w/w), 0.5% (% w/w), 0.6% (% w/w), 0.7% (% w/w), 0.8% (% w/w), 0.9% (% w/w), 1% (% w/w), 1.5% (% w/w), 2% (% w/w), 2.5% (% w/w), 3% (% w/w), 3.5% (% w/w), 4% (% w/w), 4.5% (% w/w), or 5% (% w/w) of the composition. In one embodiment, the amount of filming agent present in the composition may range between about 0.05% and about 5% (% w/w) of the composition. In another embodiment, the amount of filming agent present in the composition may range between about 0.1% and 4% (% w/w) of the composition. In an alternative embodiment, the amount of filming agent present in the composition may range between about 0.2% and about 2.5% (% w/w).

III. Surfactant

The composition of the present disclosure additionally comprises a surfactant. Any surfactant known in the art may be used in the composition of the present disclosure. For example, suitable surfactants may include non-ionic polymeric surfactants, "natural oil" esters such as palm oil and castor oil ethoxylates, long chain "detergent range" alcohol esters, or mixtures or admixtures thereof. The specific examples described below, which illustrate one embodiment of the present invention, utilize E-Z-MULSE® (Florida Chemical Co., Winterhaven, Fla.) as a surfactant. E-Z-MULSE® is a mixture of propylene glycol, castor oil ethoxylates, and detergent range alcohol ethoxylates.

Typically, a surfactant comprises between about 0.5% and about 6% (% w/w) of the composition. In a preferred embodiment, a surfactant comprises between about 1.5% and about 3.5% (% w/w) of the composition.

IV. Additional Components

In addition to the components detailed in Sections I through III, above, a variety of other compounds may optionally be added to the composition of the present disclosure without departing from the scope of the invention. For example, preservatives, antioxidants, vitamins, other nutrients and combinations thereof may also be included in the composition of the present invention.

In one embodiment, the composition may additionally comprise a preservative. Suitable preservatives include sodium benzoate, parabens, DMDM hydantoin (also known as GLYDANT®), tetrasodium ethylenediaminetetraacetic acid ("tetrasodium EDTA"), chloroallylhexaminium chloride, which is commercially purchased as DOWICIL® 200 from Dow Chemical Company, Germaben II™, Phenonip, sodium benzoate, Tinosan® SDC, and NIPAGUARD BPX®, which is commercially available from Clariant, may be added to the antimicrobial compositions to prevent germs from forming and promote stability during shelf-life. Generally, preservatives may comprise between about 0.01% to about 1% (% w/w) of the composition. Preferably, preservatives may comprise between about 0.05% to about 0.8% (% w/w) of the composition. Most preferably, preservatives may comprise between about 0.1% to about 0.4% (% w/w) of the composition.

In another embodiment, the composition may additionally comprise an antioxidant. Suitable antioxidant additives include ascorbic acid, butylated hydroxyanisole ("BHA"), butylated hydroxytoluene ("BHT"), tert-butylhydroquinone ("TBHQ"), vitamins A, C, and E and derivatives, and various plant extracts such as those containing cartenoids, tocopherols or flavonoids having antioxidant properties, may be included to increase the shelf-life or nutritionally enhance the composition. The antioxidants may have a presence at levels from about 0.01% to about 10%, preferably from about 0.05% to about 5%, and more preferably from about 0.1% to about 2% by weight of the composition.

In a further embodiment, the composition may further comprise a nutrient such as a vitamin, a mineral, an antioxidant, an omega-3 fatty acid, or an herb. Suitable vitamins include Vitamins A, C and E, which are also antioxidants, and Vitamins B and D. Examples of minerals that may be added include the salts of aluminum, ammonium, calcium, magnesium, and potassium. Suitable omega-3 fatty acids include docosahexanenoic acid ("DHA"). Herbs that may be added include basil, celery leaves, chervil, chives, cilantro, parsley, oregano, tarragon, and thyme.

V. Methods for Protecting Fish Against Infections

In another embodiment, the antimicrobial compositions disclosed herein are useful in protecting fish from infections by surrounding the fish's entire body with antimicrobial plant essential oils and sealing those oils around the fish's body with filming agents. In one embodiment, the compositions may be applied by dropper to an aquatic environment (e.g. an aquarium) in an amount effective to shield the fish from the varieties of parasites, bacterial, fungus, and protozoa that may be present in the aquatic environment and for which the composition has been selected. The compositions of the invention may be used on a variety of aquatic animals including, namely fish.

Each composition of the invention may be applied by dropper to an aquatic environment according to practices known to those skilled in the art. Administration of each composition may be intermittent in time and may be administered daily, weekly, biweekly, monthly, bimonthly, or even for longer durations of time. Preferably, the administration of the compositions is daily.

The effective amount of each composition to be applied to an animal is dependent upon the size of the aquatic environment to be treated and the number of fish living therein. For example, it is preferable to administer about 1 ml of the composition for every 5.0 gallons of water. But the amount may vary by an order of magnitude or more in some instances without departing from the scope of the invention.

When introducing elements of the present invention or the preferred embodiments(s) thereof, the articles "a," "an," "the" and "said" are intended to mean that there are one or more of the elements. The terms "comprising," "including" and "having" are intended to be inclusive and mean that there may be additional elements other than the listed elements.

As various changes could be made in the above formulations and methods without departing from the scope of the invention, it is intended that all matter contained in the above description and in the examples given below, shall be interpreted as illustrative and not in a limiting sense.

EXAMPLES

Example 1

Preparation of a Bactericidal/Fungicidal Composition

Table 1 lists the formulation of an exemplary bactericidal/fungicidal composition prepared according to the present teachings.

TABLE 1

Formulation for Bactericidal/Fungicidal Composition

| Component | Total Batch (50 gal) |
|---|---|
| d-Limonene | 28.6 fl. oz. |
| Pine oil | 7.15 fl. oz. |
| Geranium oil | 14.3 fl. oz. |
| Rosemary oil | 14.3 fl. oz. |
| Cinnamon oil | 14.3 fl. oz. |
| Chitosan | 7.12 oz. |
| EZ-MULSE ® | 129.9 fl. oz. |
| Nipaguard BPX ™ | 24.2 fl. oz. |
| BHT | 7.12 oz. |
| Polyvinylpyrrolidone K29/32 | 17.2 oz. |
| Triethylene glycol | 4.80 qts. |
| De-ionized water | Up to 50 gal. |

De-ionized water up to 35 gallons was added to a conventional mixing tank, such as a stainless steel jacketed kettle equipped with an air operated propeller mixer or a paddle mixer. The mixer was started and the dial indicating mixing speed was set to between 10 and 30. The d-Limonene and BHT were added to the tank. Mixing proceeded for approximately 10 minutes until the BHT was fully dissolved. Thereafter, the pine oil, geranium oil, cinnamon oil and rosemary oil were added to the mixing tank and mixing continued for an additional 10 minutes at the same mixing speed. Following the mixing of the plant essential oils, EZ-MULSE® was added to the tank and mixing again continued for 10 minutes at the same mixing speed. After the incorporation of the EZ-MULSE® into the composition, Nipaguard BPX™ was added to the tank and mixed at the same mixing speed for 10 minutes. Thereafter, polyvinylpyrrolidone was slowly added to the composition, followed by the triethylene glycol and the chitosan. All components were mixed together for an additional 5 minutes at the same mixing speed. The remaining amount of de-ionized water was then added in order to bring the batch up to 50 gallons. The solution was blended until a uniform milky liquid was observed.

Example 2

Preparation of a Parasitical Composition

Table 2 lists the formulation of an exemplary parasitical composition prepared according to the present teachings.

TABLE 2

Formulation for Parasitical Composition

| Component | Total Batch (50 gal) |
|---|---|
| d-Limonene | 28.6 fl. oz. |
| Neem oil | 28.6 fl. oz. |
| Manuka oil | 28.6 fl. oz. |
| Capsaicin oil | 7.15 fl. oz. |
| Chitosan | 7.12 oz. |
| EZ-MULSE ® | 129.9 fl. oz. |
| Nipaguard BPX ™ | 24.2 fl. oz. |
| BHT | 7.12 oz. |
| Polyvinylpyrrolidone K29/32 | 17.2 oz. |
| Triethylene glycol | 4.80 qts. |
| De-ionized water | Up to 50 gal. |

De-ionized water up to 35 gallons was added to a conventional mixing tank, such as a stainless steel jacketed kettle equipped with an air operated propeller mixer or a paddle mixer. The mixer was started and the dial indicating mixing speed was set to between 10 and 30. d-Limonene and BHT were added to the tank. Mixing proceeded for approximately 10 minutes until the BHT was fully dissolved. Thereafter, the neem oil, manuka oil, and capsaicin oil were each added to the mixing tank and mixing continued for an additional 10 minutes at the same mixing speed. Following the mixing of the plant essential oils, EZ-MULSE® was added to the tank and mixing again continued for 10 minutes at the same mixing speed. After the incorporation of the EZ-MULSE® into the composition, Nipaguard BPX™ was added to the tank and mixed at the same mixing speed for 10 minutes. Thereafter, polyvinylpyrrolidone was slowly added to the composition, followed by the triethylene glycol and the chitosan. All components were mixed together for an additional 5 minutes at the same mixing speed. The remaining amount of de-ionized water was then added in order to bring the batch up to 50 gallons. The solution was blended until a uniform milky liquid was observed.

Example 3

Preparation of a Protozoical Composition

Table 3 lists the formulation of an exemplary protozoical composition prepared according to the present teachings.

TABLE 3

Formulation for Protozoical Composition

| Component | Total Batch (50 gal) |
|---|---|
| d-Limonene | 28.6 fl. oz. |
| Neem oil | 28.6 fl. oz. |
| Manuka oil | 28.6 fl. oz. |
| Chitosan | 7.12 oz. |
| EZ-MULSE ® | 129.9 fl. oz. |
| Nipaguard BPX ™ | 24.2 fl. oz. |
| BHT | 7.12 oz. |
| Polyvinylpyrrolidone K29/32 | 17.2 oz. |
| Triethylene glycol | 4.80 qts. |
| De-ionized water | Up to 50 gal. |

De-ionized water up to 35 gallons was added to a conventional mixing tank, such as a stainless steel jacketed kettle equipped with an air operated propeller mixer or a paddle mixer. The mixer was started and the dial indicating mixing speed was set to between 10 and 30. d-Limonene and BHT were added to the tank. Mixing proceeded for approximately 10 minutes until the BHT was fully dissolved. Thereafter, the neem oil and manuka oil were each added to the mixing tank and mixing continued for an additional 10 minutes at the same mixing speed. Following the mixing of the plant essential oils, EZ-MULSE® was added to the tank and mixing again continued for 10 minutes at the same mixing speed. After the incorporation of the EZ-MULSE® into the composition, Nipaguard BPX™ was added to the tank and mixed at the same mixing speed for 10 minutes. Thereafter, polyvinylpyrrolidone was slowly added to the composition, followed by the triethylene glycol and the chitosan. All components were mixed together for an additional 5 minutes at the same mixing speed. The remaining amount of de-ionized water was then added in order to bring the batch up to 50 gallons. The solution was blended until a uniform milky liquid was observed.

Example 4

Establishing the Dose Ratio of the Bactericidal/Fungicidal Composition by Assessing the Toxicity on Marine Fish, Corals and Invertebrates in Saltwater The bactericidal/fungicidal composition was prepared in accordance with Example 1. The indoor experiment consisted of three (3) sets of seven (7) small covered glass aquariums of equal dimensions, each containing 20 liters of salt water. A line was drawn to indicate the water level to monitor evaporation. Each aquarium was equipped with a Tetra Whisper In Tank Filter® with the carbon removed from the cartridge. The tests were conducted under a normal photo-period with a light/dark ratio of 16:8 hours. Florescent sunlight and actinic lighting was used. The pH, temperature and specific were measured just before the experiment commenced. No sediment or gravel was used in any of the aquariums.

The test species consisted of fish, Arrow crab, Candy Cane Shrimp, Hermit crabs, and assorted corals. The test species were maintained in the same water as that being used to fill the test aquariums for one (1) week prior to the test. Water quality and illumination was the same as used in the test. The fish, corals, and invertebrates were fed as normal up to the twenty-four (24) hour period immediately preceding the test. The test fish, corals, and invertebrates were moved to the test tanks twenty-four (24) hours before the start of the test. The test species were not fed during the testing period. No treatment was administered during the test or one (1) week prior to the test.

The test species were randomly selected from the stock tanks and placed in each test tank. Each test tank received the following species: 3 fish, 1 Arrow crab, 1 Candy Cane Shrimp, 2 Hermit crabs, and 4 assorted corals. No dropped, mishandled or malformed species were used. All of the test species were added within a period of thirty (30) minutes and left to acclimatize twenty-four (24) hours before the addition of the treatment composition. Water analysis before and after the study was conducted with an Oakton pH meter, National Industrial Supply Refractometer and Cen-Tech Laser Thermometer. Tables 4 and 5 set forth the average starting water analysis and average ending water analysis, respectively.

TABLE 4

Average Starting Water Analysis

| TEMPERATURE | pH | SALINITY | OXYGEN (mg/L) | DEAD |
|---|---|---|---|---|
| 21° ± 1 C. | 8.30 | 1.022 | 6.33 | N/A |

TABLE 5

Average Ending Water Analysis

| TEMPERATURE | pH | SALINITY | OXYGEN (mg/L) | DEAD |
|---|---|---|---|---|
| 21° ± 1 C. | 8.39 | 1.022 | 7.22 | N/A |

The treatment dose each tank received was based on a dose rate of 1 ml per 5 gallons. Each tank was 5 gallons. The dosage administered to each tank is set forth in Table 6. Tank 7 in each set was marked as a control tank and was not dosed. All doses were added accurately and within a five minute period.

TABLE 6

Dosages Administered to Tanks in Test Group

| 1.0x | 2.0x | 3.0x | 4.0x | 5.0x | 6.0x | Control |
|---|---|---|---|---|---|---|
| Tank 1 | Tank 2 | Tank 3 | Tank 4 | Tank 5 | Tank 6 | Tank 7 |
| 1.0 ml | 2.0 ml | 3.0 ml | 4.0 ml | 5.0 ml | 6.0 ml | 0.0 ml |

The tanks were observed for a total of ninety-six (96) hours. Observations were recorded twice daily to include twenty-four (24), forty-eight (48), seventy-two (72) and ninety-six (96) hours. All tanks were observed hourly for the first eight (8) hours of the test. Any test species that were found dead in the tanks were recorded with the tank species, number and the time it was found. The dead were removed from the tanks as soon as possible. A post-mortem examination was done if possible. All abnormal behavior of the test species was also noted.

No fish mortalities or damage to the fish were found in any of the groups, at any of the dosage levels. Microscopic examination of all fish indicated no damage to any organs. There were no mortalities or damage among the invertebrates at any of the dosage levels in any of the groups. There were no mortalities among the corals but most of the corals did respond negatively by contracting at the normal dosage but recovered within twenty-four (24) hours. Those at the higher dosage levels (from two (2) times to six (6) times the normal dosage) experienced more long term contraction, requiring required up to fourteen (14) days to recover. Splitting the normal dosage in half on day one to 0.50 ml, then 0.50 ml on day two was found to reduce the coral reaction observed at the normal dosage.

Example 5

Establishing the Dose Ratio of the Parasitical Composition by Assessing the Toxicity on Marine Fish, Corals and Invertebrates in Saltwater The parasitical composition was prepared in accordance with Example 2. The indoor experiment consisted of three (3) sets of seven (7) small covered glass aquariums of equal dimensions, each containing 20 liters of salt water. A line was drawn to indicate the water level to monitor evaporation. Each aquarium was equipped with a Tetra Whisper In Tank Filter® with the carbon removed from the cartridge. The tests were conducted under a normal photo-period with a light/dark ratio of 16:8 hours. Florescent sunlight and actinic lighting was used. The pH, temperature and specific were measured just before the experiment commenced. No sediment or gravel was used in any of the aquariums.

The test species consisted of fish, Arrow crab, Candy Cane Shrimp, Hermit crabs, and assorted corals. The test species were maintained in the same water as that being used to fill the test aquariums for one (1) week prior to the test. Water quality and illumination was the same as used in the test. The fish, corals, and invertebrates were fed as normal up to the twenty-four (24) hour period immediately preceding the test. The test fish, corals, and invertebrates were moved to the test tanks twenty-four (24) hours before the start of the test. The test species were not fed during the testing period. No treatment was administered during the test or one (1) week prior to the test.

The test species were randomly selected from the stock tanks and placed in each test tank. Each test tank received the following species: 3 fish, 1 Arrow crab, 1 Candy Cane Shrimp, 2 Hermit crabs, and 4 assorted corals. No dropped, mishandled or malformed species were used. All of the test species were added within a period of thirty (30) minutes and left to acclimatize twenty-four (24) hours before the addition of the treatment composition. Water analysis was conducted with an Oakton pH meter, National Industrial Supply Refractometer and Cen-Tech Laser Thermometer. All test species were visually examined after the ninety sixth (96) hour. Stained tissue preparations of the fish were made of the gills, liver and spleen for microscopic examination. Tables 7 and 8 set forth the average starting water analysis and average ending water analysis, respectively.

TABLE 7

| Average Starting Water Analysis | | | | |
| --- | --- | --- | --- | --- |
| TEMPERATURE | pH | SALINITY | OXYGEN (mg/L) | DEAD |
| 21° ± 1 C. | 8.10 | 1.022 | 6.20 | N/A |

TABLE 8

| Average Ending Water Analysis | | | | |
| --- | --- | --- | --- | --- |
| TEMPERATURE | pH | SALINITY | OXYGEN (mg/L) | DEAD |
| 21° ± 1 C. | 8.00 | 1.023 | 6.47 | N/A |

The treatment dose each tank received was based on a dose rate of 1 ml per 5 gallons. Each tank was 5 gallons. The dosage administered to each tank is set forth in Table 9. Tank 7 of each set was marked as a control tank and was not dosed. All doses were added accurately and within a five minute period.

TABLE 9

| Dosages Administered To Tanks in Test Group | | | | | | |
| --- | --- | --- | --- | --- | --- | --- |
| 1.0x | 2.0x | 3.0x | 4.0x | 5.0x | 6.0x | Control |
| Tank 1 | Tank 2 | Tank 3 | Tank 4 | Tank 5 | Tank 6 | Tank 7 |
| 1.0 ml | 2.0 ml | 3.0 ml | 4.0 ml | 5.0 ml | 6.0 ml | 0.0 ml |

The tanks were observed for a total of ninety six (96) hours. Observations were recorded twice daily to include twenty-four (24), forty-eight (48), seventy-two (72) and ninety-six (96) hours. All tanks were observed hourly for the first eight (8) hours of the test. Any test species that were found dead in the tanks were recorded with the tank species, number and the time it was found. The dead were removed from the tanks as soon as possible. A post-mortem examination was done if possible. All abnormal behavior of the test species was also noted.

No fish mortalities or damage to the fish were found in any of the groups, at any of the dosage levels. Microscopic examination of all fish indicated no damage to any organs. There were no mortalities or damage among the invertebrates at any of the dosage levels in any of the groups. There were no mortalities among the corals but most of the corals did respond negatively by contracting at the normal dosage but recovered within twenty-four (24) hours. Those at the higher dosage levels (from two (2) times to six (6) times the normal dosage) experienced more long term contraction, requiring required up to fourteen (14) days to recover. Splitting the normal dosage in half on day one to 0.50 ml, then 0.50 ml on day two was found to reduce the coral reaction observed at the normal dosage.

Example 6

Establishing the Dose Ratio of the Protozoical Composition by Assessing the Toxicity on Marine Fish, Corals and Invertebrates in Saltwater The protozoical composition was prepared in accordance with Example 3. The indoor experiment consisted of three (3) sets of seven (7) small covered glass aquariums of equal dimensions, each containing 20 liters of salt water. A line was drawn to indicate the water level to monitor evaporation. Each aquarium was equipped with a Tetra Whisper In Tank Filter® with the carbon removed from the cartridge. The tests were conducted under a normal photo-period with a light/dark ratio of 16:8 hours. Florescent sunlight and actinic lighting was used. The pH, temperature and specific were measured just before the experiment commenced. No sediment or gravel was used in any of the aquariums.

The test species consisted of fish, Arrow crab, Candy Cane Shrimp, Hermit crabs, and assorted corals. The test species were maintained in the same water as that being used to fill the test aquariums for one (1) week prior to the test. Water quality and illumination was the same as used in the test. The fish, corals, and invertebrates were fed as normal up to the twenty-four (24) hour period immediately preceding the test. The test fish, corals, and invertebrates were moved to the test tanks twenty-four (24) hours before the start of the test. The test species were not fed during the testing period. No treatment was administered during the test or one (1) week prior to the test.

The test species were randomly selected from the stock tanks and placed in each test tank. Each test tank received the following species: 3 fish, 1 Arrow crab, 1 Candy Cane Shrimp, 2 Hermit crabs, and 4 assorted corals. No dropped, mishandled or malformed species were used. All of the test species were added within a period of thirty minutes and left to acclimatize twenty-four (24) hours before the addition of the treatment composition. Water analysis was conducted with an Oakton pH meter, National Industrial Supply Refractometer and Cen-Tech Laser Thermometer. All test species were visually examined after the ninety-sixth (96) hour. Stained tissue preparations of the fish were made of the gills, liver and spleen for microscopic examination. Tables 10 and 11 set forth the average starting water analysis and average ending water analysis, respectively.

TABLE 10

| Average Starting Water Analysis | | | | |
| --- | --- | --- | --- | --- |
| TEMPERATURE | pH | SALINITY | OXYGEN (mg/L) | DEAD |
| 21° ± 1 C. | 8.39 | 1.022 | 7.22 | N/A |

TABLE 11

| Average Ending Water Analysis | | | | |
| --- | --- | --- | --- | --- |
| TEMPERATURE | pH | SALINITY | OXYGEN (mg/L) | DEAD |
| 21° ± 1 C. | 8.40 | 1.022 | 7.20 | N/A |

The treatment dose each tank received was based on a dose rate of 1 ml per 5 gallons. Each tank was 5 gallons. The dosage administered to each tank is set forth in Table 12. Tank 7 of each set was marked as a control tank and was not dosed. All doses were added accurately and within a five minute period.

TABLE 12

| Dosages Administered to Tanks in Test Group | | | | | | |
| --- | --- | --- | --- | --- | --- | --- |
| 1.0x | 2.0x | 3.0x | 4.0x | 5.0x | 6.0x | Control |
| Tank 1 | Tank 2 | Tank 3 | Tank 4 | Tank 5 | Tank 6 | Tank 7 |
| 1.0 ml | 2.0 ml | 3.0 ml | 4.0 ml | 5.0 ml | 6.0 ml | 0.0 ml |

The tanks were observed for a total of ninety-six (96) hours. Observations were recorded twice daily to include twenty-four (24), forty-eight (48), seventy-two (72) and ninety-six (96) hours. All tanks were observed hourly for the first eight (8) hours of the test. Any test species that were found dead in the tanks were recorded with the tank species, number and the time it was found. The dead were removed from the tanks as soon as possible. A post-mortem examination was done if possible. All abnormal behavior of the test species was also noted.

No fish mortalities or damage to the fish were found in any of the groups, at any of the dosage levels. Microscopic examination of all fish indicated no damage to any organs. There were no mortalities or damage among the invertebrates at any of the dosage levels in any of the groups. There were no mortalities among the corals but most of the corals did respond negatively by contracting at the normal dosage but recovered within twenty-four (24) hours. Those at the higher dosage levels (from two (2) times to six (6) times the normal dosage) experienced more long term contraction, requiring required up to fourteen (14) days to recover. Splitting the normal dosage in half on day one to 0.50 ml, then 0.50 ml on day two was found to reduce the coral reaction observed at the normal dosage.

Example 7

Establishing the Dose Ratio of the Antimicrobial Composition by Assessing the Toxicity on Freshwater Fish Each of the compositions set forth in Examples 1-3 were prepared and tested to determine appropriate dose ratio. The indoor experiment consisted of two (2) sets (set 1 and set 2) of ten (10) small covered glass aquariums of equal dimensions, each containing 20 liters of local tap water which was slowly filtered through carbon to remove any organic content. A line was drawn to indicate the water level to monitor evaporation. The water was heated in each aquarium until it reached a temperature of 25° C.±1 degree. The water was left in the aquariums for twenty-four (24) hours to equilibrate with an airline lightly aerating the water to ensure adequate oxygen levels.

The tests were conducted under a normal photo-period with a light/dark ratio of 16:8 hours. Florescent sunlight and actinic lighting was used. The pH, temperature, hardness, alkalinity, and dissolved oxygen were measured just before the experiment commenced. No sediment or gravel was used in any aquarium.

The test species consisted of Corydoras (*Paleatus*) Catfish and Neon Tetras (*Paracheirodon innesi*). The test species were maintained in the same water as that being used to fill the test aquariums for two (2) weeks prior to the test. Water quality and illumination was the same as used in the test. The fish were fed as normal up to the twenty-four (24) hour period immediately preceding the test. The test fish were moved to the test tanks twenty-four (24) hours before the start of the test. The test fish were not fed during the testing period. The fish were examined and certified free of any disease or visible malformation. No treatment was administered during the test or two (2) weeks prior to the test.

Ten (10) Catfish were selected from the stock tank and one was placed in each aquarium comprising set 1. Ten (1) Neon Tetras were selected from the stock tank and one was placed in each aquarium comprising set 2. No dropped, mishandled or malformed species were used. All of the fish were added within a period of thirty (30) minutes and left to acclimatize twenty-four (24) hours before the addition of the treatment composition.

The treatment dose each tank received was based on a dose rate of one (1) ml per five (5) gallons (18.92 liters). Each tank was five (5) gallons. The dosage administered to each tank is set forth in Tables 13 and 14. Tank 10 of each set was marked as a control tank and was not dosed. All doses were added accurately and within a five minute period.

TABLE 13

| Dosages Administered to Tanks in Set 1 (Catfish) | | | | | | | | | |
| --- | --- | --- | --- | --- | --- | --- | --- | --- | --- |
| 1.0x | 2.0x | 3.0x | 4.0x | 5.0x | 6.0x | 7.0x | 8.0x | 9.0x | Control |
| Tank 1 | Tank 2 | Tank 3 | Tank 4 | Tank 5 | Tank 6 | Tank 7 | Tank 8 | Tank 9 | Tank 10 |
| 1.0 ml | 2.0 ml | 3.0 ml | 4.0 ml | 5.0 ml | 6.0 ml | 7.0 ml | 8.0 ml | 9.0 ml | 0.0 ml |

TABLE 14

| Dosages Administered to Tanks in Set 2 (Neon Tetras) | | | | | | | | | |
|---|---|---|---|---|---|---|---|---|---|
| 1.0x | 2.0x | 3.0x | 4.0x | 5.0x | 6.0x | 7.0x | 8.0x | 9.0x | Control |
| Tank 1 1.0 ml | Tank 2 2.0 ml | Tank 3 3.0 ml | Tank 4 4.0 ml | Tank 5 5.0 ml | Tank 6 6.0 ml | Tank 7 7.0 ml | Tank 8 8.0 ml | Tank 9 9.0 ml | Tank 10 0.0 ml |

The tanks were observed for a total of ninety-six (96) hours. Observations were recorded twice daily to include twenty-four (24), forty-eight (48), seventy-two (72) and ninety-six (96) hours. All tanks were observed hourly for the first eight (8) hours of the test. Any test species that were found dead in the tanks were recorded with the tank species, number and the time it was found. The dead were removed from the tanks as soon as possible. A post-mortem examination was done if possible. All abnormal behavior of the test species was also noted.

No fish mortalities or damage to the fish were found in any of the groups, at any of the dosage levels (at one to nine times the normal instructed dose). Microscopic examination of all fish indicated no damage to any organs. Normal dosage levels did not do any damage to the fish.

Water analysis was conducted with an Oakton pH meter, Micro 10 Spectrophotometer and Hach water analysis procedures for hardness and alkalinity. All test fish were visually examined after the ninety sixth (96) hour. Stained tissue preparations of the fish were made of the gills, liver and spleen for microscopic examination. Tables 15 and 16 set forth the average starting water analysis and average ending water analysis, respectively.

TABLE 15

| Average Starting Water Analysis | | | | | |
|---|---|---|---|---|---|
| TEMPERATURE | pH | HARDNESS (mg/L) | ALKALINITY (mg/L) | OXYGEN (mg/L) | DEAD |
| 26° ± 1 C. | 7.98 | 120 | 119 | 7.00 | N/A |

TABLE 16

| Average Ending Water Analysis | | | | | |
|---|---|---|---|---|---|
| TEMPERATURE | pH | HARDNESS (mg/L) | ALKALINITY (mg/L) | OXYGEN (mg/L) | DEAD |
| 26° ± 1 C. | 7.99 | 119 | 121 | 7.03 | N/A |

Example 8

Effectiveness of Parasitical Composition

The parasitical composition prepared as in accordance with Example 2 was used to treat a parasitical outbreak in an aquarium. The aquarium contained baby fish, newly born livebearers, and live plants, all of a variety of species.

The composition was administered to the tank as per normal dosage levels—one (1) ml per five (5) gallons (18.92 liters). Treatment was administered over the course of 5 days.

After 3 days of treatment, 95% cure was evidenced. Full cure was evidenced by the end of 5 days. None of the fish or plants exhibited any sensitivity to the product and there were no mortalities during or following treatment.

One skilled in the art would readily appreciate that the methods and compositions described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for reducing the incidence of microbial infections in fish, the method comprising dispensing an antimicrobial composition into an aquatic environment, the composition comprising between about 0.2% and about 1.6% (% w/w) of at least one plant essential oil, between about 0.1% and about 0.6% (% w/w) of at least one filming agent, between about 3% and about 5% (% w/w) of a plasticizer, and between about 2% and about 6% (% w/w) of a surfactant.

2. The method of claim 1, wherein the antimicrobial composition comprises a filming agent selected from the group consisting of chitosan, hydroxypropyl methyl cellulose, triethylene glycol, polyvinylpyrrolidone, polyvinyl alcohol-polyethylene glycol copolymers, basic polymethacrylate and combinations thereof.

3. The method of claim 2, wherein the filming agent is a combination of chitosan, triethylene glycol, and polyvinylpyrrolidone.

4. The method of claim 1, wherein the antimicrobial agent is dispensed daily, weekly, biweekly, monthly, bimonthly, or for longer durations of time.

5. The method of claim 4, wherein the antimicrobial agent is dispensed daily.

6. The method of claim 1, wherein between 0.5 ml and 9 ml of the composition is administered for every 5.0 gallons of water.

7. The method of claim 6, wherein 1 ml of the composition is administered for every 5.0 gallons of water.

8. The method of claim 1, wherein the desired amount is dispensed all at once or in multiple doses.

9. The method of claim 1, wherein the composition is dispensed by dropper.

10. The method of claim 1, wherein the aquatic environment is saltwater or fresh water.

11. The method of claim 1, wherein the fish are adult, baby, or newly born.

12. The method of claim 1, wherein the antimicrobial composition is administered to treat an existing microbial infection.

13. A method for reducing the incidence of bacterial infections in fish, the method comprising administering an effective amount of an anti-bacterial composition to an aquatic environment, the composition comprising between about 0.3% and about 1.3% (% w/w) of at least one plant essential oil, between about 0.1% and about 5% (% w/w) of at least one filming agent, and between about 3% and about 5% (% w/w) of a surfactant.

14. A method for reducing the incidence of parasitical infections in fish, the method comprising administering an effective amount of an anti-parasitical composition to an aquatic environment, the composition comprising between about 0.5% and about 1.5% (% w/w) of at least one plant essential oil, between about 0.1% and about 5% (% w/w) of at least one filming agent, and between about 3% and about 5% (% w/w) of a surfactant.

15. A method for reducing the incidence of protozoal infections in fish, the method comprising administering an effective amount of an anti-protozoal composition to an aquatic environment, the composition comprising between about 0.5% and about 1.3% (% w/w) of at least one plant essential oil, between about 0.1% and about 5% (% w/w) of at least one filming agent, and between about 3% and about 5% (% w/w) of a surfactant.

* * * * *